United States Patent [19]

Nagasawa et al.

[11] Patent Number: 4,816,562
[45] Date of Patent: Mar. 28, 1989

[54] NOVEL SUBSTRATE FOR PLASMA KALLIKREIN AND A METHOD FOR MEASURING BIOLOGICAL COMPONENTS USING THE SAME

[75] Inventors: Takeshi Nagasawa, Urawa; Yoshio Nakamura, Koriyama; Kenji Tani, Koriyama; Katsumasa Kuroiwa, Koriyama, all of Japan

[73] Assignee: Nitto Boseki Co., Ltd., Fukushima, Japan

[21] Appl. No.: 933,753

[22] Filed: Nov. 21, 1986

[30] Foreign Application Priority Data

Nov. 26, 1985 [JP] Japan ................. 60-265389

[51] Int. Cl.⁴ ............................. C07K 5/08
[52] U.S. Cl. ............................. 530/331; 530/802
[58] Field of Search ............................. 530/802, 331

[56] References Cited

U.S. PATENT DOCUMENTS 4,622,389 11/1986 Nagasawa et al. ............ 530/802
4,650,753 3/1987 Nagasawa et al. ............ 530/802

*Primary Examiner*—Delbert R. Phillips
*Attorney, Agent, or Firm*—Bert J. Lewen; Henry Sternberg

[57] ABSTRACT

Novel compounds represented by the following general formula (1) and salts thereof:

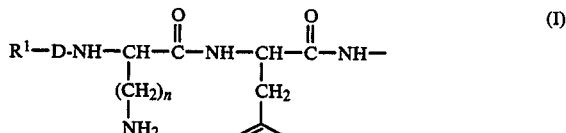

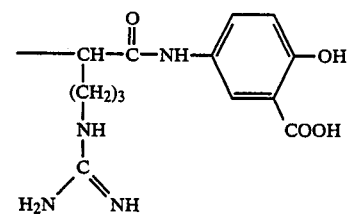

wherein n represents an integer of 3 to 4, $R^1$ represents

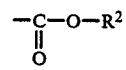

or $-SO_2R^2$, and $R^2$ represents optionally branched lower alkyl group having 1 to 6 carbon atoms, phenyl group, benzyl group or tolyl group, which are useful as substrate for use in the measurement of biological components; a substrate for use in the measurement of biological component which comprises said novel compound or salt thereof; and a method for measuring biological component which comprises using said substrate.

5 Claims, No Drawings

NOVEL SUBSTRATE FOR PLASMA KALLIKREIN AND A METHOD FOR MEASURING BIOLOGICAL COMPONENTS USING THE SAME

FIELD OF THE INVENTION AND RELATED ART STATEMENT

The present invention relates to a novel color-forming and fluorescent substrate for plasma kallikrein and plasma kallikrein-like enzymes. The substrate of the present invention is much superior to the hitherto reported substrates in selectivity. Accordingly, it is usable in the quantitiative analyses of plasma kallikrein, and it is particularly suitable for use in studying the reactions in which plasma kallikrein is formed, inhibited or consumed and in measuring the factors participating in these reactions, such as the measurement of plasma prekallikrein, plasma kallikrein inhibitor and the XII factor.

RELATED ART

In 1954, Shermy et al. [J. B. C., 208, 85, 105 (1954)] synthesized arginine esters such as TAMe (Tos-Arg-OMe) and the like and used them as a substrate in the measurement of esterase activity of thrombin. This was the first introduction of synthetic substrate into coagulation and fibrinolysis reactions. However, this was disadvantageous in that the ester-hydrolyzing activity of the arginine esters did not coincide with their coagulating activity and the substrates were poor in specificity and sensitivity. As the result of the recent progress in the peptide chemistry, however, a peptide substrate having an amino acid structure resembling that of the thrombin-cleaved site of fibrinogen, i.e. Bz-Phe-Val-Arg-PNA (S-2160), was synthesized by Bloembach et al. [Thromb. Research, 1, 267-278 (1972)], and it has gradually become used in researches and tests because the enzyme-chemical spectroscopic analysis utilizing the yellow color produced from the enzymatically liberated p-nitroaniline (PNA) is easy to practise and the reagents are easy to prepare.

Kallikrein is the so-called quinine-liberating enzyme which acts upon the kininogen present in the $\alpha_2$-globulin fraction of blood to liberate quinine. In the normal state, plasma kellikrein exists in the form of prekallikrein which is an inert precursor. The concentration of prekallikrein in human blood is usually constant, and its individual difference is relatively small. Its concentration decreases in special diseases, such as serious acute hepatitis, chronic diseases of digestive tract, chronic nephritis, Addison's disease, dystonia of the sympathetic nervous system, etc. An increase in its concentration is found in the early stage of acute pancreatitis, acute infections, Cushing's syndrome, etc. Since the in-blood concentration of prekallikrein changes in diseased persons either temporarily or permanently, a simple and exact method for measuring the concentration of plasma prekallikrein has a great meaning, if it is possible.

A number of methods have hitherto been developed regarding the measurement of kallikrein activity. Today, prekallikrein is measured by activating it with an activator and then measuring the resulting kallikrein. Thus, prekallikrein is activated with trypsin or Hageman factor to form kallikrein, and then the latter is determined; either (1) biologically or (2) chemically by the use of a synthetic substrate. The former method (biological method) includes the measurement of drop in blood pressure in the carotid artery, the measurement of increase in blood flow and the method using extirpated smooth muscle, etc. Although it has a high reliability, it is disadvantageous in that it requires high technics and experiences. On the other hand, the latter method (chemical method) is a measurement of esterase activity using a synthetic substrate such as BAEE (Bz-Arg-OEt), TAME (Tos-Arg-OMe), etc. Its procedure is simple and it is widely applicable.

Now, a synthetic substrate for use in enzymatic measurements should satisfy the following four important requirements: high sensitivity to enzyme, high specificity to enzyme, high solubility in water or biological test medium, and easy detectability of decomposition product.

Among these requirements, the "high specificity to the enzyme to be measured" is particularly important.

When prekallikrein, kallikrein inhibitor and the like present in blood is measured by the use of a color-forming substrate, an exact measurement is generally unexpectable so far as cross reaction with proteolytic enzymes other than kallikrein such as plasmin, thrombin, Xa factor, urokinase, glandular kallikrein and the like, of which existence in blood is expected, takes place.

Among the synthetic substrates for plasma kallikrein which have been developed up to date, H-D-Pro-Phe-Arg-PNA (S-2302 AB Kabi Diagnostical) [Claeson, G. et al., Haemostasis, 7, 62 (1978)] can be referred to as the best one. However, it is yet unsatisfactory in the point of substrate specificity. That is to say, it is known that this synthetic substrate reacts not only with plasma kallikrein but also with other proteolytic enzymes, i.e. plasmin, thrombin, Xa factor and glandular kallikrein, to a considerable extent.

Further, the above-mentioned method of colorimetrically determining the yellow color of the resulting p-nitroaniline, as in the case of the above-mentioned substrate, cannot be free from the influence of plasma components.

OBJECT AND SUMMARY OF THE INVENTION

The present inventors conducted a developmental study of a novel substrate for plasma kallikrein with the aim of overcoming the faults of prior substrates. As the result, a substrate having excellent properties with which the above-mentioned disadvantages can be overcome to a marked extent and the above-mentioned four requirements can be satisfied was discovered.

The novel color-producing and fluorescent substrate of the invention is represented by the following general formula:

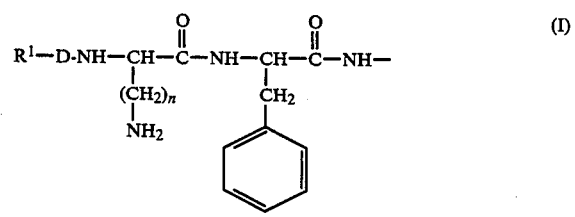

-continued

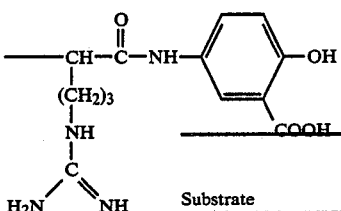

wherein n represents an integer of 3 to 4; $R^1$ represents

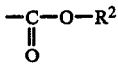

or $-SO_2-R^2$; and $R^2$ represents optionally branched lower alkyl group having 1 to 6 carbon atoms such as methyl, ethyl, propyl, butyl, pentyl and the like or phenyl group or benzyl group or tolyl group. It is particularly characterized by using 3-carboxy-4-hydroxyanilide as the chromophore. Having very hydrophilic hydroxyl and carboxyl groups as its chromophores, this substrate has outstanding solubility characteristics into water. Its typical use consists in using the substrate [I] as a substrate for the measurement of plasma kallikrein. The principle of the measurement consists in converting the 3-carboxy-4-hydroxyaniline formed as the main product into a colored substance according to the pentacyanoamine ferroate method or the oxidative condensation with an appropriate coupler, followed by colorimetrically determining the colored substance. Alternatively, it is also possible to specifically measure the plasma kallikrein acitivity by a fluorescence analysis at an exciting wavelength of 328 nm and a fluorescence wavelength of 540 nm.

As has been mentioned above, the characteristic feature of this substrate consists in its excellent substrate specificity to plasma kallikrein. In Table 1, there are shown the relative reactivities between the novel substrate PS-2203 (produced by Nitto Boseki K.K.), S-2302 (AB Kabi Diagnostica: reference smaple) and PS-2203N (Z-D-Orn-Phe-Arg-PNA; a synthetic reference sample having the same amino acid sequence as in the above-mentioned novel substrate and having PNA as chromophore) and the enzymes dealing with their coagulation and fibrinolysis, i.e. plasma kallikrein (HPK), thrombin (TH), plasmin (PL), Xa factor (FXa), glandular kallikrein (HGK) and urokinase (UK), taking that in Z-D-Orn-Phe-Arg-PNA (PS-2203N) as 100. Table 1 demonstrates the following facts. Thus, the CHA type novel substrate has outstandingly low reactivities with thrombin, plasmin, Xa factor and glandular kallikrein. Thus, its reactivity is 2% with thrombin, 14% with plasmin, 4% with Xa factor and 15% with glandular kallikrein. This means that the substrate of the invention is markedly improved in selectivity as compared with S-2302 of which reactivity is 269% with thrombin, 48% with plasmin, 169% with Xa factor, 169% with glandular kallikrein and 50% with urokinase.

TABLE 1

Relative reactivities with various enzymes

| Substrate | Enzyme | | | | | |
|---|---|---|---|---|---|---|
|  | HPK | HGK | TH | PL | FXa | UK |
| S-2302 (Reference substrate) | 131 | 169 | 269 | 48 | 169 | 50 |
| H—D-Pro—Phe—Arg—PNA | (0.325) | (0.021) | (0.152) | (0.121) | (0.389) | (0.011) |
| PS-2203N (Reference substrate) | 100 | 100 | 100 | 100 | 100 | 100 |
| Z—D-Orn—Phe—Arg—PNA | (0.249) | (0.013) | (0.056) | (0.250) | (0.230) | (0.021) |
| PS-2203 (Substrate of the invention) | 59 | 15 | 2 | 14 | 4 | 0 |
| Z—D-Orn—Phe—Arg—CHA | (0.331) | (0.005) | (0.007) | (0.079) | (0.022) | (0.0) |

Initial substrate concentration $S_0 = 2$ mM, the figures in the parenthesis denote measured O.D. values.

DETAILED DESCRIPTION OF PREFERRED EMBODIMENTS

As has been mentioned above, the compound of the present invention is quite excellent as a substrate for plasma kallikrein.

The use of the compound of the invention is the use as a substrate for measurement of plasma kallikrein activity. Thus, plasma kallikrein activity can be measured by reacting said substrate upon plasma kallikrein in a buffer having a pH value of 8.0 to 9.0, converting the resulting 3-carboxy-4-hydroxyaniline to an appropriate colored substance, and then colorimetrically analyzing the latter quantitatively. Alternatively, it is also possible to determine the plasma kallikrein activity by a fluorescence analysis at an exciting wavelength of 328 nm and a fluorescence wavelength of 540 nm. The present compound can be used as a substrate as it is.

As the method for the conversion into colored substance, the pentacyanoamine ferroate method and the oxidative condensation with a coupler can be referred to. As said coupler, aniline compounds such as N,N-diethylaniline can be used when the color is produced in an acidic atmosphere. When the color is produced in an alkaline atmosphere, phenol, naphthol, o-cresol, o-ethylphenol and the like are usable as the coupler.

As the oxidant for the oxidative condensation, hydrogen peroxide, persulfuric acid and other various substances can be used, among which meta-periodic acid is particularly preferable.

If 3-carboxy-4-hydroxyaniline is converted to an appropriate colored substance, the wavelength of maximum absorption of the resulting colored substance is distributed in the range of 560 nm to 770 nm. The color is stable and its dependence on temperature is quite small, so that this method is suitable for the measurement of plasma kallikrein activity. Further, the method of the invention is superior in the point of color forming sensibility, too. Thus, $\epsilon = 10,600$ at 405 nm (wavelength of usual measurements) in the case of p-nitroaniline, while $\epsilon = 21,500$ at $\lambda = 700$ nm in the pentaamine ferroate method. In the color formation by oxidative condensation, $\epsilon = 29,000$ at $\lambda = 645$ nm in the case of o-ethylphenol and $\epsilon = 21,600$ at $\lambda = 615$ nm in the case of 2,6-xylenol. These quite high values of absorbance also makes the measurement according to the invention quite advantageous.

As one of the characteristic features of the invention, there can be referred to that the result of the measurement is hardly influenced by the contaminative substances present in biological samples. This is due to that the measurement using p-nitroanilide compound is carried out at a wavelength not higher than 560 nm while the measurement according to the invention is carried out at a wavelength not lower than 560 nm, and therefore the measurement of the invention is not influenced by the contaminative substances present in sample. This, in addition to the high specificity of the substrate itself, enables to obtain exact result of measurement.

It is apparent from the description presented above that the compound of the invention is much superior as a substrate for the measurement of plasma kallikrein activity to the prior ones.

The compound of the invention represented by formula (I) can be synthesized according to the method well known in the peptide chemistry.

As the α-amino-protecting group, carbobenzoxy group, t-butyloxycarbonyl group and related groups thereof, such as p-methoxy, p-nitro and p-methoxyphenylazolcarbobenzoxy derivatives thereof, are advantageously usable.

For protecting the δ-guadinyl group of arginine, the protection using nitro group and the method of protonation are advantageously employable. The coupling of two amino acids or the coupling of dipeptide and amino acid can be practised by activating the α-carboxyl group. For example, N-hydroxysuccinic imide, p-nitrophenol, trichlorophenol, 4,6-dimethylpyrimidyl-2-thiol, mixed acid anhydrides and the like can be used for this purpose. The above-mentioned activation into ester derivative is preferably carried out in the presence of a carbodiimide, such as N,N-dicyclohexylcarbodiimide (DCC). In the case of mixed acid anhydrides, monoalkyl chlorocarbonate, such as isobutyl chloroformate, are advantageously usable.

The substrate can be synthesized by first bonding a chromophore to arginyl group and thereafter successively carrying out the coupling. Alternatively, it is also possible to synthesize the substrate by first synthesizing N-terminated dipeptide fragment itself and then bonding it to an arginyl group having a chromophore.

The compound of the invention is usable in the form of acid adduct salt, too. As the acid used for the formation of said acid adduct salt, mineral acids such as hydrochloric acid, sulfuric acid and the like and organic acids such as acetic and the like are preferably used.

Next, the present invention will be illustrated in more detail with reference to the following examples in no limitative way.

Meanings of the abbreviations used in the examples and conditions of thin layer chromatography and gel permeation chromatography carried out in the examples are as follows.

(1) Abbreviations

Arg=arginine
Phe=phenylalanine
Lys=lysine
Orn=ornithine
Z=benzyloxycarbonyl
BOC=t-butyloxycarbonyl
i-BOC=i-butyloxycarbonyl
MOC=methyloxycarbonyl
SBz=benzenesulfonyl
Tos=p-toluenesulfonyl
OSu=succinic acid imide ester
—pNA=p-nitroanilide
—CHA=3-carboxy-4-hydroxyanilide
DMF=dimethylformamide
NEM=N-ethylmorpholine
TLC=thin layer chromatography
MeOH=methanol
AcOH=acetic acid
BuOH=n-butanol
AcOEt=ethyl acetate
GPC=gel permeation chromatography
(Note: All the amino acids are L-isomers, unless otherwise referred to.)

(2) Conditions of thin layer chromatography

The TLC analyses were carried out with Silica Gel $F_{254}$ (manufactured by Merk) plate and the following solvents:
$R_{f1}$ n-BuOH:AcOH:$H_2O$=4:1:1
$R_{f2}$ n-BuOH:AcOH:$H_2O$=4:1:2
$R_{f3}$ n-BuOH:AcOH:$H_2O$=4:1:5

(3) The gel permeation chromatography was carried out with Toyopearl HW40F (trade name; polyvinyl gel, manufactured by Toyo Soda Kogyo K.K.).

EXAMPLE 1

Synthesis of Z-D-Orn-Phe-Arg-CHA

I. BOC-Arg-CHA.HCl

Into 1,392 ml of MDF was dissolved 381.1 g (1.16 moles) of BOC-Arg-OH.HCl.$H_2O$. After adding 151 ml of NEM, 152.3 ml of isobutyl chloroformate was dropwise added thereto at $-20°$ C. After reacting the mixture for 10 minutes, a solution of 219.8 g (1.16 moles) of 5-aminosalicylic acid hydrochloride and 301.6 ml of NEM in 928 ml of DMF was dropwise added to the reaction mixture at a temperature of $-15°$ C. to $-10°$ C. After dropping it, the resulting mixture was reacted first at that temperature for 3 hours and thereafter at room temperature for 15 hours. After the reaction, the DMF was distilled off under reduced pressure, and the residue was dissolved into a mixture of 464 ml of MeOH and 332 ml of n-BuOH. Then, 3,300 ml of AcOH was added to the solution, the mixture was washed with two 2,160 ml portions of cold 5% hydrochloric acid saturated with sodium chloride, and then it was dried over anhydrous magnesium sulfate. After dryness, the magnesium sulfate was filtered off and the solvent was distilled off under reduced pressure. Thus, 464.8 g (89.9%) of BOC-Arg-CHA.HCl was obtained.

$R_{f1}$=0.64, m.p. 225.0° C. (decomposition).
$[\alpha]_D^{20}$ −10.7° (C=1, MeOH).

| Elementary analyses $C_{18}H_{28}N_5O_6Cl.H_2O$ | | | |
| --- | --- | --- | --- |
| | C | H | N |
| Found | 46.71 | 6.60 | 14.90 |
| Calculated | 46.60 | 6.52 | 15.10 |

II. BOC-Phe-Arg-CHA.HCl

Into a mixture consisting of 1,093 ml of 2N HCl/AcOH and a small quantity of MeOH was dissolved 243.7 g (0.55 mole) of BOC-Arg-CHA.HCl, and the resulting solution was reacted at room temperature for one hour. After the reaction, 1,093 ml of isopropyl alcohol was added, and the product was re-precipitated in AcOEt. The deposited crystalline product was collected by filtration and dried to obtain 156.2 g (74.3%) of H-Arg-CHA.2HCl.

$R_{f3}$=0.15, m.p. 240.5° C. (decomposition).

$[\alpha]_D^{20} +53.5°$ (C=1, H$_2$O).

Into a mixture consisting of 412.2 ml of DMF and 99.8 ml (0.77 mole) of NEM was dissolved 146.8 g (0.38 mole) of H-Arg-CHA.2HCl. Then, BOC-Phe-SDP was added at 0° to 5° C. and the mixture was reacted at room temperature for 18 hours. After the reaction, the solvent was distilled off under reduced pressure, and the residue was dissolved into a mixture consisting of 1.5 liters of AcOEt and a small quantity of MeOH. Then, it was washed successively with three 1.5 liter portions of cold 5% hydrochloric acid saturated with sodium chloride and two 1.5 liter portions of saturated aqueous solution of sodium chloride, and then decolorized and dried with anhydrous magnesium sulfate and active charcoal. After dryness, the magnesium sulfate and active charcoal were filtered off and the solvent was distilled off under reduced pressure. Thus, 224.2 g (99.5%, a foamed material) of BOC-Phe-Arg-CHA.HCl was obtained.

$R_{f2}$=0.61.

$[\alpha]_D^{20} -14.8°$ (MeOH, C=1).

| Elementary analyses C$_{27}$H$_{37}$N$_6$O$_7$Cl.$\frac{3}{2}$H$_2$O | | | |
|---|---|---|---|
| | C | H | N |
| Found | 53.52 | 6.69 | 13.55 |
| Calculated | 53.46 | 6.40 | 13.85 |

III. Z-D-Orn(BOC)-Phe-Arg-CHA.HCl

Into 538 ml of 2N HCl/AcOH was dissolved 79.8 g (0.13 mole) of BOC-Phe-Arg-CHA.HCl. After reacting it at room temperature for one hour, the deposited matter was collected by filtration, washed with AcOH and ether and dried to obtain 41.8 g (58.7%) of H-Phe-Arg-CHA.2HCl.

$R_{f2}$=0.36, m.p.=240.5°-242.5° C.

$[\alpha]_D^{20} -9.0°$ (MeOH, C=1).

| Elementary analyses C$_{22}$H$_{30}$N$_6$O$_5$Cl$_2$.3/2H$_2$O | | | |
|---|---|---|---|
| | C | H | N |
| Found | 47.19 | 5.70 | 14.90 |
| Calculated | 47.49 | 5.98 | 15.10 |

Into 5.7 ml (8.6 mmoles) of 1.5N NEM/DMF was dissolved 2.3 g (4.3 mmoles) of H-Phe-Arg-CHA.2HCl. After adding 2.0 g (4.3 mmoles) of Z-D-Orn(BOC)-OSU at a temperature of 0° to 5° C., the resulting mixture was reacted at room temperature for 18 hours. After the reaction, the solvent was distilled off under reduced pressure, the residue was dissolved into a mixture consisting of 4.3 ml of MeOH and 43 ml of AcOEt, and it was washed with two 20 ml portions of cold 5% hydrochloric acid saturated with sodium chloride. Thus, a crystalline product began to deposit slowly. After allowing the AcOEt layer overnight while cooling it, the deposited crystal was collected by filtration and dried. Thus, 3.2 g (88.8%) of Z-D-Orn(BOC)-Phe-Arg-CHA.HCl was obtained.

$R_{f2}$=0.81, mp.=191°-220° C. (decomposition).

$[\alpha]_D^{20} -11.0°$ (MeOH, C=1).

| Elementary analyses C$_{40}$H$_{53}$N$_8$O$_{10}$Cl.H$_2$O | | | |
|---|---|---|---|
| | C | H | N |
| Found | 56.06 | 6.54 | 12.81 |
| Calculated | 55.90 | 6.45 | 13.04 |

IV. Z-D-Orn-Phe-Arg-CHA.2HCl

Into 5.2 ml (10.4 mmoles) of 2N HCl/AcOH was dissolved 2.3 g (2.6 mmoles) of Z-D-Orn(BOC)-Phe-Arg-CHA.HCl. After reacting it at room temperature for 2 hours, the product was precipitated in dry ether and the deposited crystalline product was collected by filtration and dried. Thus, crude Z-D-Orn-Phe-Arg-CHA.2HCl was obtained. It was purified by means of Toyopearl HW40F column with 30% AcOH as a developing solvent. Thus, 1.52 g (74.9%) of Z-D-Orn-Phe-Arg-CHA.2HCl was obtained.

$R_{f2}$=0.44, m.p.=165°-192° C.

$[\alpha]_D^{20} -7.0°$ (MeOH, C=0.5).

| Elementary analyses C$_{35}$H$_{46}$N$_8$O$_8$Cl$_2$.H$_2$O | | | |
|---|---|---|---|
| | C | H | N |
| Found | 53.11 | 6.30 | 13.74 |
| Calculated | 52.83 | 6.08 | 14.08 |

EXAMPLE 2

Synthesis of Tos-D-Lys-Phe-Arg-CHA.2HCl

Into 75 ml of MeOH was dissolved 8.9 g (10.4 mmoles) of Z-D-Lys(BOC)-Phe-Arg-CHA.HCl. After adding 1 gram of palladium black, it was catalytically reduced at 30° C. for 8 hours. After the reaction, the catalyst was filtered off and the solvent was distilled off under reduced pressure. Thus, 6.4 g (85.3%; a foamed product) of H-D-Lys(BOC)-Phe-Arg-CHA.2HCl was obtained.

$R_{f2}$=0.49, m.p.=180.5°-205° C.

Into a mixture consisting of 5 ml of DMF and 0.57 ml (4.1 mmoles) of triethylamine was dissolved 1.0 g (1.8 mmoles) of H-D-Lys(BOC)-Phe-Arg-CHA.2HCl. After adding 0.28 g (1.45 mmoles) of p-toluenesulfonyl chloride at a temperature of 0° to 5° C., the mixture was reacted at room temperature for 18 hours. After the reaction, the solvent was distilled off under reduced pressure and the residue was dissolved into a mixture consisting of 1.3 ml of MeOH and 13 ml of AcOEt. The solution thus formed was washed successively with two 5 ml portions of cold 5% hydrochloric acid saturated with sodium chloride and two portions of saturated aqueous solution of sodium chloride, after which it was dried over anhydrous magnesium sulfate and decolorized with active charcoal. After dryness, the magnesium sulfate and active charcoal were filtered off and the solvent was distilled off under reduced pressure. Thus, 1.3 g of crude Tos-D-Lys(BOC)-Phe-Arg-CHA.HCl was obtained. It was purified by means of Toyopearl HW40F column with MeOH as a developing solvent. Thus, 1.0 g (91.4%) of Tos-D-Lys(BOC)-Phe-Arg-CHA.HCl was obtained.

$R_{f2}$=0.79, m.p.=198°-206° C. (decomposition).

$[\alpha]_D^{20} +15.0°$ (MeOH, C=1).

| Elementary analyses C$_{40}$H$_{55}$N$_8$O$_{10}$SCl.3/2H$_2$O | | | |
|---|---|---|---|
| | C | H | N |
| Found | 53.21 | 6.32 | 12.40 |
| Calculated | 53.23 | 6.48 | 12.42 |

II. Tos-D-Lys-Phe-Arg-CHA.2HCl

Into 1.7 ml (3.5 mmoles) of 2N HCl/AcOH was dissolved 0.77 g (0.88 mmoles) of Tos-D-Lys(BOC)-Phe-Arg-CHA.HCl. After reacting it at room temperature for 2 hours, the reaction mixture was reprecipitated in dry ether and the deposited crystalline product was collected by filtration and dried. Thus, 0.70 g of crude Tos-D-Lys-Phe-Arg-CHA.2HCl was obtained. It was purified by means of Toyopearl HW40F column with 30% AcOH as a developing solvent. Thus, 0.48 g (67.6%) of Tos-D-Lys-Phe-Arg-CHA.2HCl was obtained.

$R_{f2}=0.39$, m.p.$=177°-191°$ C.
$[\alpha]_D^{20}-7.0°$ (MeOH, C=0.5).

| Elementary analyses $C_{35}H_{48}N_8O_8SCl_2.\frac{1}{2}H_2O$ | | | |
|---|---|---|---|
| | C | H | N |
| Found | 51.45 | 6.19 | 13.62 |
| Calculated | 51.22 | 6.02 | 13.65 |

EXAMPLE 3

The following substrates were synthesized by the same procedures as have been mentioned above.

| | | m.p. (°C.) | $R_{f2}$ | $[\alpha]_D^{20}$ (MeOH: C = 0.5) |
|---|---|---|---|---|
| PS-2200 | Z—D-Lys—Phe—Arg—CHA.2HCl | 156–174 | 0.47 | −4.0° |
| PS-2202 | i-BOC—D-Lys—Phe—Arg—CHA.2HCl | 171–177 | 0.50 | −10.0° |
| PS-2204 | MOC—D-Lys—Phe—Arg—CHA.2HCl | 172–191 | 0.38 | −17.0° |
| PS-2206 | SBz—D-Lys—Phe—Arg—CHA.2HCl | 179–188 | 0.37 | +10.0° |

| | Elementary analyses | |
|---|---|---|
| | Found (%) | Calculated (%) |
| PS-2200 | | $C_{36}H_{48}N_8O_8Cl_2.H_2O$ |
| C | 53.23 | 53.40 |
| H | 6.13 | 6.22 |
| N | 13.51 | 13.84 |
| PS-2202 | | $C_{33}H_{50}N_8O_8Cl_2.H_2O$ |
| C | 51.33 | 51.09 |
| H | 6.84 | 6.76 |
| N | 14.30 | 14.45 |
| PS-2204 | | $C_{30}H_{44}N_8O_8Cl_2.3/2H_2O$ |
| C | 48.83 | 48.52 |
| H | 6.46 | 6.38 |
| N | 14.74 | 15.09 |
| PS-2206 | | $C_{34}H_{46}N_8O_8SCl_2.H_2O$ |
| C | 50.83 | 50.62 |
| H | 6.06 | 5.87 |
| N | 13.57 | 13.89 |

EXAMPLE 4

The specificities of the novel substrates synthesized above were examined by reacting them with various enzymes.

(1) Substrate solution: 2 mmoles/liter $H_2O$
(2) Buffer solution: Concentrations of Tris, NaCl and $CaCl_2$ and pH value of reaction for every enzyme were as follows:

| | Plasma kallikrein (HPK) | Glandular kallikrein (HGK) | Thrombin (TH) | Plasmin (PL) | Xa factor (FXa) | Urokinase (UK) |
|---|---|---|---|---|---|---|
| Tris (mmoles) | 50 | 50 | 50 | 50 | 50 | 50 |
| NaCl (mmoles) | 150 | 150 | 150 | 150 | 250 | 150 |
| $CaCl_2$ (mmoles) | 0 | 0 | 0 | 0 | 5 | 0 |
| pH (25° C.) | 9.0 | 9.0 | 8.5 | 7.8 | 8.3 | 8.2 |

(3) Enzymes used

| | Orgin | Maker | Lot No. | Unit |
|---|---|---|---|---|
| Plasma kallikrein | Human | AB Kabi Diagnostica | 3740152 | 0.12 U/ml |
| Glandular kallikrein | Human urine | Green Cross | 1003SM | 0.1 U/ml |
| Thrombin | Bovine | Mochida Pharmaceutical | 65146 | 4.0 NIH/ml |
| Plasmin | Human | Green Cross | PL-35 | 0.25 CU/ml |
| FXa | Bovine | Sigma | 73F-9450 | 0.4 U/ml |
| Urokinase | Human | Mochida Pharmaceutical | 2A-139 | 1,000 U/ml |

(4) Reaction stopper (PNA): 10% AcOH
(5) Reaction-stopping color-forming reagent: Pentaamine ferroate (pH = 10.4)

Procedure of the Measurement

Into a silicone-treated test tube made of hard glass or a plastic were introduced 0.3 ml of a buffer solution and 0.1 ml of an enzyme reagent. After preheating them for 5 minutes in a thermostated bath kept at 37° C., 0.1 ml of substrate solution was added and an enzyme reaction was carried out at 37° C. for 5 minutes. When an exact five minutes had passed, 2.0 ml of the reaction stopper or the reaction-stopping color-forming reagent was added to stop the enzyme reaction, and subsequently the reaction mixture was allowed to stand at 37° C. for 10 minutes. Then, absorbance was measured at 405 nm or 700 nm.

The results were as shown in Table 2.

TABLE 2

| Comparison of substrate-specificities | | | | | | | |
|---|---|---|---|---|---|---|---|
| | | HPK | HGK | TH | PL | FXa | UK |
| Reference Examples 1-2] Substrate | | | | | | | |
| 1. S-2302 | H—D-Pro—Phe—Arg—PNA | 0.325 | 0.021 | 0.152 | 0.121 | 0.389 | 0.011 |
| 2. PS-2203N | Z—D-Orn—Phe—Arg—PNA | 0.250 | 0.013 | 0.056 | 0.250 | 0.230 | 0.021 |
| Compounds of This Invention [3-8] | | | | | | | |
| 3. PS-2200 | Z—D-Lys—Phe—Arg—CHA | 0.316 | 0.010 | 0.009 | 0.094 | 0.046 | 0.002 |
| 4. PS-2202 | i-BOC—D-Lys—Phe—Arg—CHA | 0.245 | 0.006 | 0.005 | 0.128 | 0.040 | 0.0 |
| 5. PS-2203 | Z—D-Orn—Phe—Arg—CHA | 0.331 | 0.005 | 0.007 | 0.079 | 0.022 | 0.0 |
| 6. PS-2204 | MOC—D-Lys—Phe—Arg—CHA | 0.301 | 0.016 | 0.010 | 0.107 | 0.046 | 0.0 |
| 7. PS-2205 | Tos—D-Lys—Phe—Arg—CHA | 0.255 | 0.014 | 0.015 | 0.158 | 0.010 | 0.0 |
| 8. PS-2206 | SBZ—D-Lys—Phe—Arg—CHA | 0.234 | 0.010 | 0.007 | 0.094 | 0.016 | 0.0 |

Initial substrate concentration $S_0$ = 2.0 mM; the numerical figures denote absorbance (O.D). The wavelength of measurement was 405 nm in Nos. 1-2 and 700 nm in Nos. 3-8.

What is claimed is:

1. A compound represented by the general formula:

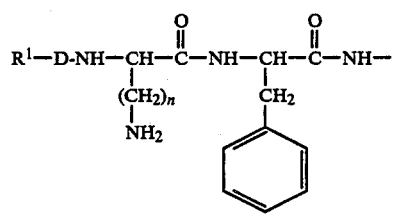

-continued

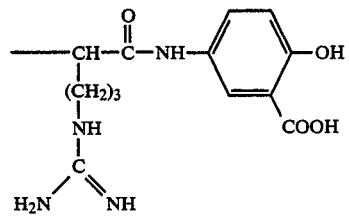

wherein n is 3 or 4; $R^1$ is

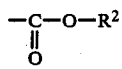

or —$SO_2R^2$; and $R^2$ is an optionally branched lower alkyl having 1 to 6 carbon atoms, a phenyl, a benzyl or a tolyl group; or a salt of one of such groups.

2. A compound according to claim 1 wherein $R^1$ is benzyloxycarbonyl, i-butyloxycarbonyl or methyloxycarbonyl, and n is 3 or 4.

3. A compound according to claim 2 wherein n is 3 and $R^1$ is benzyloxycarbonyl.

4. A compound according to claim 1 wherein $R^1$ is benzenesulfonyl or p-toluenesulfonyl, and n is 3 or 4.

5. A compound according to claim 4 wherein n is 4.

* * * * *